US009149252B2

(12) United States Patent  
Tashiro et al.

(10) Patent No.: US 9,149,252 B2  
(45) Date of Patent: Oct. 6, 2015

(54) ULTRASOUND DIAGNOSTIC APPARATUS, METHOD OF TRANSMITTING AND RECEIVING ULTRASONIC WAVE, AND PROGRAM FOR TRANSMITTING AND RECEIVING ULTRASONIC WAVE

(75) Inventors: Rika Tashiro, Ashigara-kami-gun (JP); Yukiya Miyachi, Ashigara-kami-gun (JP); Kimito Katsuyama, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 478 days.

(21) Appl. No.: 13/408,505

(22) Filed: Feb. 29, 2012

(65) Prior Publication Data

US 2012/0226164 A1     Sep. 6, 2012

(30) Foreign Application Priority Data

Mar. 3, 2011    (JP) .................. 2011-046725

(51) Int. Cl.
- *A61B 8/14*     (2006.01)
- *A61B 8/08*     (2006.01)
- *G01S 15/89*    (2006.01)

(52) U.S. Cl.
CPC ............. *A61B 8/0841* (2013.01); *A61B 8/5253* (2013.01); *G01S 15/899* (2013.01); *G01S 15/8927* (2013.01)

(58) Field of Classification Search
USPC ........................... 600/407, 437, 461, 443–447  
See application file for complete search history.

(56) References Cited

U.S. PATENT DOCUMENTS

| 6,048,312 | A  | * | 4/2000 | Ishrak et al. ............ 600/443 |
| 6,692,439 | B1 | * | 2/2004 | Walker et al. ............ 600/443 |

(Continued)

FOREIGN PATENT DOCUMENTS

| JP | 9-28708 A    | 2/1997 |
| JP | 2004215987 A | 8/2004 |
| JP | 2010029374 A | 2/2010 |
| JP | 2011024886 A | 2/2011 |

OTHER PUBLICATIONS

Notification of Reasons for Refusal, dispatched Aug. 27, 2013, issued in corresponding JP Application No. 2012-033957, 6 page in English and Japanese.

(Continued)

*Primary Examiner* — Joel F Brutus  
(74) *Attorney, Agent, or Firm* — Sughrue Mion, PLLC

(57) ABSTRACT

An ultrasound diagnostic apparatus includes plural ultrasound transducers which perform transmission and reception of ultrasonic waves toward a target site of a subject containing a puncture needle. A method of transmitting and receiving an ultrasonic wave uses the ultrasound transducers. The apparatus and the method form an ultrasonic beam to be transmitted from a transmit aperture set on the ultrasound transducers, acquire information relating to a specular-reflective component of the ultrasonic beam in the puncture needle, set a first receive aperture different from the transmit aperture set on the ultrasound transducers on the basis of the information relating to the specular-reflective component of the ultrasonic beam, and process an ultrasonic echo signal received by the ultrasound transducers using the first receive aperture.

10 Claims, 8 Drawing Sheets

(56) References Cited

U.S. PATENT DOCUMENTS

| | | | |
|---|---|---|---|
| 2002/0173719 A1* | 11/2002 | Zhao et al. | 600/437 |
| 2003/0100832 A1* | 5/2003 | Criton et al. | 600/443 |
| 2004/0144176 A1 | 7/2004 | Yoden | |
| 2006/0241456 A1 | 10/2006 | Karasawa | |
| 2008/0139937 A1* | 6/2008 | Nohara et al. | 600/443 |
| 2008/0242989 A1 | 10/2008 | Koide | |
| 2010/0022883 A1 | 1/2010 | Satoh | |

OTHER PUBLICATIONS

Communication, dated Jul. 11, 2012, issued in corresponding EP Application No. 12156866.1, 6 pages.

The First Office Action, dated Dec. 31, 2014, issued in corresponding CN Application No. 201210048195.8, 19 pages in English and Chinese.

* cited by examiner

ULTRASOUND DIAGNOSTIC APPARATUS, METHOD OF TRANSMITTING AND RECEIVING ULTRASONIC WAVE, AND PROGRAM FOR TRANSMITTING AND RECEIVING ULTRASONIC WAVE

BACKGROUND OF THE INVENTION

The present invention relates to an ultrasound diagnostic apparatus which diagnoses the inside of a subject, such as a human body, using an ultrasound probe having a plurality of ultrasound transducers, a method of transmitting and receiving an ultrasonic wave which transmits and receives an ultrasonic wave from an ultrasound probe to a subject, a program for transmitting and receiving an ultrasonic wave which causes a computer to execute a plurality of steps of the method of transmitting and receiving an ultrasonic wave, that is, a plurality of steps of transmitting and receiving an ultrasonic wave, and a computer readable recording medium having recorded therein the program for transmitting and receiving an ultrasonic wave. In particular, the present invention relates to a technique for allowing paracentesis or the like in which a puncture needle is inserted into a subject while viewing an ultrasound image.

An ultrasound vibrator which is used in an ultrasound diagnostic apparatus is formed by integrating a plurality of ultrasound transducers (vibrators). A transmit aperture and a receive aperture are set on each of a plurality of ultrasound transducers at the time of transmission and reception of an ultrasonic wave, and the delay time (delay amount) of each of the transmission output of the transmit aperture and the reception output of the receive aperture of each ultrasound transducer is appropriately controlled for each ultrasound transducer. An ultrasonic transmission beam and an ultrasonic reception beam are respectively synthesized to obtain ultrasound reception image data.

An ultrasound diagnostic apparatus is known which has a structure (puncture adapter) in which a puncture needle can be attached to an ultrasound probe such that a biopsy on a specific site in a subject as a measurement target can be easily performed using a dedicated puncture needle. In this apparatus, a guideline when the puncture needle is inserted is displayed on a display. If the ultrasound diagnostic apparatus is operated using the ultrasound probe while the puncture needle is inserted into the subject in accordance with the guideline, an operator can simultaneously confirm an image in the subject and the motion of the puncture needle on the display, thereby performing safe paracentesis (biopsy, drainage, or the like).

However, in the ultrasound diagnostic apparatus of the related art, there is a problem that the intensity of an echo signal from the puncture needle is weak depending on the entrance angle of the puncture needle, and the image of the puncture needle is difficult to view on the display. As a method of solving this problem, a technique is known in which the surface of the tip of the puncture needle is processed roughly (roughened). However, this technique has a problem in that an echo signal from other than the tip of the puncture needle is not sufficiently intensified, and it is not sufficient to intensify the echo signal itself.

For this reason, JP 9-28708 A describes a technique which, when a puncture needle is inserted into a subject, adjusts the transmission beam direction of an ultrasound scan beam at substantially a right angle with respect to the entrance path of the puncture needle, and controls the delay amount of the output of each ultrasound transducer such that the transmission beam focal point position of each scan beam is in the vicinity of the position of the puncture needle.

SUMMARY OF THE INVENTION

On the other hand, in the technique described in JP 9-28708 A, with the direction and focal point control of the transmission beam of the ultrasound scan beam, an ultrasonic echo signal of a target line, such as a line of the puncture needle entering the subject, can be intensified, but there is a problem in that transmission and reception control is significantly complicated.

In the technique described in JP 9-28708 A, the directionality of the reception beam of the ultrasound scan beam, or the like is not sufficiently taken into consideration, and there is a problem in that the effect of improving the intensity of the echo signal from the puncture needle is not sufficient. For example, in the technique described in JP 9-28708 A, there is a problem in that, if the insertion angle of the puncture needle increases, the specular-reflective component of the transmission beam is out of the receive aperture set on the plurality of ultrasound transducers at the time of reception, and the echo signal from the puncture needle may not be sufficiently received, thereby causing the intensity of the echo signal to be weakened.

Further, there is also a problem that since the transmission of an ultrasound scan beam is a steer transmission inclined with respect to the surface of the subject, the quality of the image other than of the puncture needle deteriorates even where the visibility of the puncture needle can be improved.

In the technique described in JP 9-28708 A, since the ultrasonic echo signal from the puncture needle is not directly stored, there is a problem in that, at the time of an image process after reception, the intensity of the ultrasonic echo signal from the puncture needle may not be improved, and thus the visibility of the puncture needle may not be improved.

The invention has been finalized in consideration of the above-described situation, and an object of the invention is to provide an ultrasound diagnostic apparatus, a method of transmitting and receiving an ultrasonic wave, a program for transmitting and receiving an ultrasonic wave, and a recording medium capable of increasing the intensity of an ultrasonic echo signal from a puncture needle and improving visibility of the puncture needle.

To achieve the above object, an ultrasound diagnostic apparatus according to a first aspect of the invention is configured to comprise a plurality of ultrasound transducers which performs transmission and reception of ultrasonic waves toward a target site of a subject containing a puncture needle; transmission control means for forming an ultrasonic beam to be transmitted from a transmit aperture set on the plurality of ultrasound transducers; acquisition means for acquiring information relating to a specular-reflective component of the ultrasonic beam in the puncture needle; reception control means for setting a first receive aperture different from the transmit aperture set on the plurality of ultrasound transducers on the basis of the information relating to the specular-reflective component of the ultrasonic beam; and reception signal processing means for processing an ultrasonic echo signal received by the plurality of ultrasound transducers using the first receive aperture.

Preferably, the acquisition means acquires the information relating to the specular-reflective component from the positional relationship between the plurality of ultrasound transducers and the puncture needle.

Preferably, the acquisition means acquires the information relating to the specular-reflective component from the insertion angle of the puncture needle inserted into the subject with respect to the plurality of ultrasound transducers.

It is preferable that the transmission control means forms the ultrasonic beam to be deflected and that the acquisition means acquires the information relating to the specular-reflective component from the insertion angle of the puncture needle and the deflection angle of the ultrasonic beam.

Preferably, the reception signal processing means performs a weighting process on the ultrasonic echo signal to highlight the specular-reflective component.

Preferably, the reception signal processing means further includes a storage unit which temporarily stores the ultrasonic echo signal.

It is preferable that the reception signal processing means further includes a storage unit which temporarily stores the ultrasonic echo signal, performs weighting processing for enhancing a subject tissue component on the ultrasonic echo signal, and synthesizes this ultrasonic echo signal on which weighting processing for enhancing a subject tissue component has been performed and an ultrasonic echo signal on which weighting processing for enhancing the specular-reflective component has been performed.

Preferably, the reception control means sets the first receive aperture so as to contain ultrasound transducers located on a side opposite with respect to the transmit apertures from an insertion position at which the puncture needle is introduced into a subject.

It is preferable that the reception signal control means sets a second receive aperture different from the first receive aperture and synthesizes the ultrasonic echo signals obtained using the first receive aperture and the second receive aperture in accordance with multiple times of transmission by the transmit aperture.

It is preferable that the reception control means sets a plurality of division receive apertures discontinuously divided on the plurality of ultrasound transducers as the first receive aperture, that there is at least one ultrasound transducer not used as receive aperture between two adjacent division receive apertures, and that the reception signal processing means synthesizes the ultrasonic echo signals obtained using the plurality of division receive apertures for one transmission by the transmit apertures.

To achieve the above object, a method of transmitting and receiving an ultrasonic wave according to a second aspect of the invention is configured as a method of transmitting and receiving an ultrasonic wave toward a target site of a subject containing a puncture needle using a plurality of ultrasound transducers, the method comprising the steps of forming an ultrasonic beam to be transmitted from a transmit aperture set on the plurality of ultrasound transducers; transmitting the formed ultrasonic beam toward the target site of the subject; acquiring information relating to a specular-reflective component of the ultrasonic beam in the puncture needle; setting a first receive aperture different from the transmit aperture on the plurality of ultrasound transducers on the basis of the information relating to the specular-reflective component of the ultrasonic beam; receiving an ultrasonic echo signal of the ultrasonic beam by plurality of ultrasound transducers using the set first receive aperture; and processing the ultrasonic echo signal received by the plurality of ultrasound transducers using the first receive aperture.

To achieve the above object, a program for transmitting and receiving an ultrasonic wave according to a third aspect of the invention is configured as a program for transmitting and receiving an ultrasonic wave for causing a computer to execute the individual steps of transmitting and receiving an ultrasonic wave according to the above-mentioned second aspect of the invention as steps of transmitting and receiving an ultrasonic wave toward a target site of a subject containing a puncture needle using a plurality of ultrasound transducers. Thus, this aspect is a program for transmitting and receiving an ultrasonic wave which causes a computer to execute a plurality of steps for transmitting and receiving an ultrasonic wave toward a target site of a subject containing a puncture needle using a plurality of ultrasound transducers, wherein the plurality of steps includes the steps of forming an ultrasonic beam to be transmitted from a transmit aperture set on the plurality of ultrasound transducers, transmitting the formed ultrasonic beam toward the target site of the subject, acquiring information relating to a specular-reflective component of the ultrasonic beam in the puncture needle, setting a first receive aperture different from the transmit aperture on the plurality of ultrasound transducers on the basis of the information relating to the specular-reflective component of the ultrasonic beam, receiving an ultrasonic echo signal of the ultrasonic beam by the plurality of ultrasound transducers using the set first receive aperture, and processing the ultrasonic echo signal received by the plurality of ultrasound transducers using the first receive aperture.

To achieve the above object, a recording medium according to a fourth aspect of the invention is configured as a computer readable recording medium on which the program for transmitting and receiving an ultrasonic wave according to the above-mentioned third aspect of the invention is recorded.

According to the invention, it is possible to increase the intensity of the echo signal from the puncture needle and to improve the visibility of the puncture needle.

DETAILED DESCRIPTION OF THE INVENTION

Hereinafter, an ultrasound diagnostic apparatus, a method of transmitting and receiving an ultrasonic wave, a program for transmitting and receiving an ultrasonic wave, and a recording medium according to the invention will be described in detail on the basis of preferred embodiments shown in the accompanying drawings.

Embodiment 1

Figure 1:
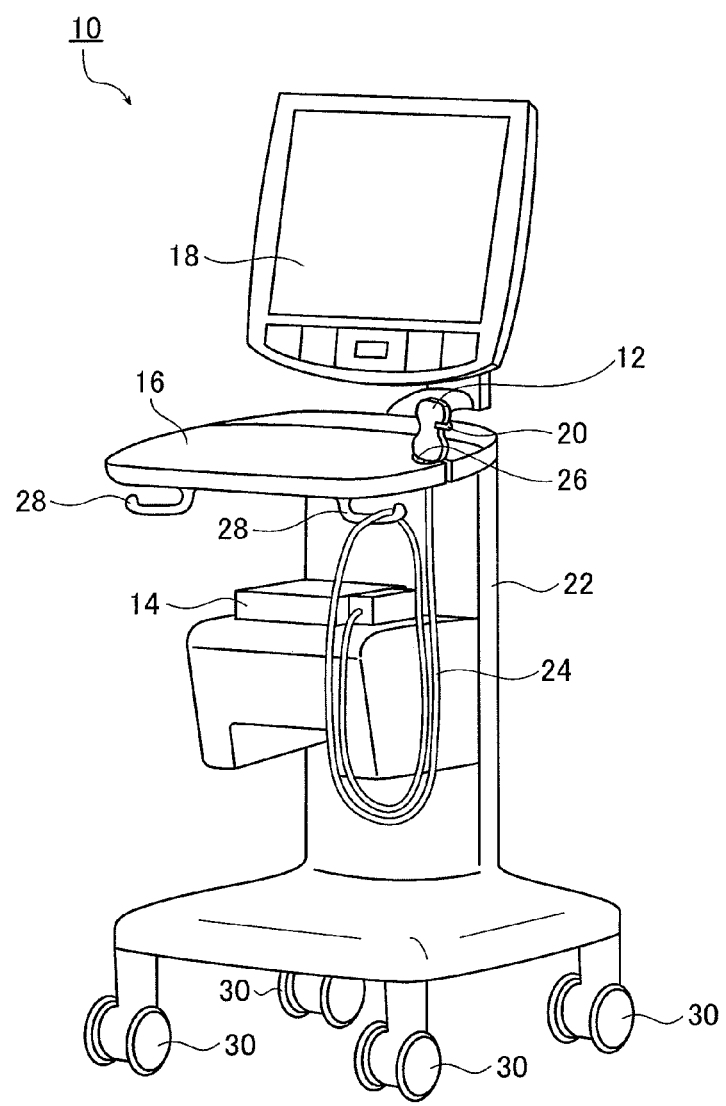
FIG. 1 is a perspective view showing an example of the main configuration of an ultrasound diagnostic apparatus according to Embodiment 1 of the invention.

FIG. 1 is a perspective view showing an example of the main configuration of an ultrasound diagnostic apparatus according to Embodiment 1 of the invention which executes a method of transmitting and receiving an ultrasonic wave according to the invention. Here, a case will be described where an ultrasound probe serving as a probe, an ultrasound diagnostic apparatus body which performs control of the ultrasound probe and analysis of an obtained ultrasonic echo signal, and synthesizes an ultrasound diagnostic image, and a display which displays a synthesized image are separately provided. A puncture adapter is attached to the ultrasound probe.

As shown in FIG. 1, an ultrasound diagnostic apparatus 10 according to Embodiment 1 of the invention executes a method of transmitting and receiving an ultrasonic wave according to the invention, and includes an ultrasound probe (hereinafter, simply referred to as a probe) 12, an ultrasound diagnostic apparatus body (hereinafter, simply referred to as an apparatus body) 14, an input unit 16, and a display 18. The ultrasound diagnostic apparatus 10 of this embodiment also includes a puncture adapter 20 which is used in a state of being attached to the probe 12. The ultrasound diagnostic apparatus 10 is configured so as to be easily movable by a cart 22.

The probe 12 is a probe in which transmission and reception of an ultrasonic wave are performed by a plurality of ultrasound transducers 13 of a one-dimensional or two-dimensional transducer array, and is used in a state where an array portion at the tip thereof having a plurality of ultrasound transducers 13 arranged thereon abuts on the surface of a human subject. Each ultrasound transducer 13 transmits an ultrasonic wave toward the subject on the basis of an activation signal to be applied, receives an ultrasonic echo reflected by the subject, and outputs a reception signal.

Each ultrasound transducer 13 is constituted by a vibrator in which electrodes are formed at both ends of a piezoelectric material (piezoelectric body), such as piezoelectric ceramic represented by PZT (Pb (lead) zirconate titanate) or a piezoelectric polymer represented by PVDF (polyvinylidene difluoride). If a pulsed or continuous-wave voltage is applied across the electrodes of the vibrator, the piezoelectric body expands and contracts. With the expansion and contraction, pulsed or continuous ultrasonic waves are produced from the vibrators, and the ultrasonic waves are synthesized to form an ultrasonic beam. When receiving the propagating ultrasonic waves, the vibrators expand and contract to produce electric signals. The electric signals are outputs as the ultrasonic reception signals.

As the type of the ultrasound probe 12, there are various types, such as a convex type, a linear scan type, and a sector scan type.

The probe 12 is connected to the apparatus body 14 by a cable 24, and the operation thereof is controlled by the apparatus body 14.

The detachable and replaceable puncture adapter 20 is attached to the probe 12.

The puncture adapter 20 is attached to the probe 12, and serves as a guide which allows a puncture needle to be inserted into a target site of the subject, such as a human subject, at a specific angle. Specifically, the puncture needle moves along a puncture provided in the puncture adapter 20 to move in a specific insertion direction set in advance, and the tip of the puncture needle is inserted into the target site of the subject. In the puncture adapter 20, the size of the usable puncture needle, the insertion angle at which the puncture needle is inserted into the human subject, the adjustment range, the insertion position, the insertion path, or the like differs depending on the type. The puncture adapter 20 is replaced, thereby changing the size of the usable puncture needle, the insertion angle, the range, the insertion position, the insertion path, or the like. In the case of the puncture adapter 20 in which the size of the usable puncture needle and the insertion angle are defined in advance, a storage unit may be provided in the puncture adapter 20, and information relating to the size of the usable puncture needle and the insertion angle may be stored in the storage unit in advance as puncture adapter information.

The apparatus body 14 has a function of performing overall control of the operations of the respective units of the ultrasound diagnostic apparatus 10. In the apparatus body 14, an ultrasonic wave is transmitted and received by the probe 12, and a tomographic image is produced from a received echo and displayed on the display 18. The apparatus body 14 produces a B-mode image or an M-mode image as a tomographic image and displays the B-mode image or the M-mode image on the display 18 in real time. The detailed configuration of the apparatus body 14 will be described below.

The input unit 16 includes a keyboard, a pointing device, or various buttons or dials for inputting various kinds of information. An operator, such as a physician or a technician, operates the ultrasound diagnostic apparatus 10 using the input unit 16. For example, the operator designates various setting values relating to the operation mode of the ultrasound diagnostic apparatus 10 according to a site under observation using the input unit 16 or changes the depth of the focus of the ultrasonic beam transmitted from the probe 12. The operator designates a region of interest (ROI) using the input unit 16. The operator inputs puncture adapter information (insertion angle) of the puncture adapter 20 using the input unit 16. When information relating to the size of the usable puncture needle and the insertion angle is stored in the storage unit of the puncture adapter 20 in advance, it is not necessary to input in the input unit 16.

The display 18 is, for example, a raster scan-type LCD or the like, and displays an ultrasound image as a moving image or a still image on the basis of analog-converted image signals output from the apparatus body 14.

In this embodiment, respective components of the ultrasound diagnostic apparatus 10 are supported by the cart 22. That is, the apparatus body 14 is placed in the cart 22 and supported by the cart 22. The input unit 16 and the display 18 are attached to the upper part of the cart 22. The probe 12 is held in a probe holder 26 which is provided on the side of the cart 22, to which the input unit 16 is attached. The cable 24 which connects the probe 12 to the apparatus body 14 is held in a hook 28 which is provided on the back of the cart 22, to which the input unit 16 is attached.

The cart 22 includes four casters 30 which are used to move the ultrasound diagnostic apparatus 10.

Although in this embodiment, the cart 22 which supports the respective components of the ultrasound diagnostic apparatus 10 is provided so as to move the ultrasound diagnostic apparatus 10, the invention is not limited thereto.

Figure 2:
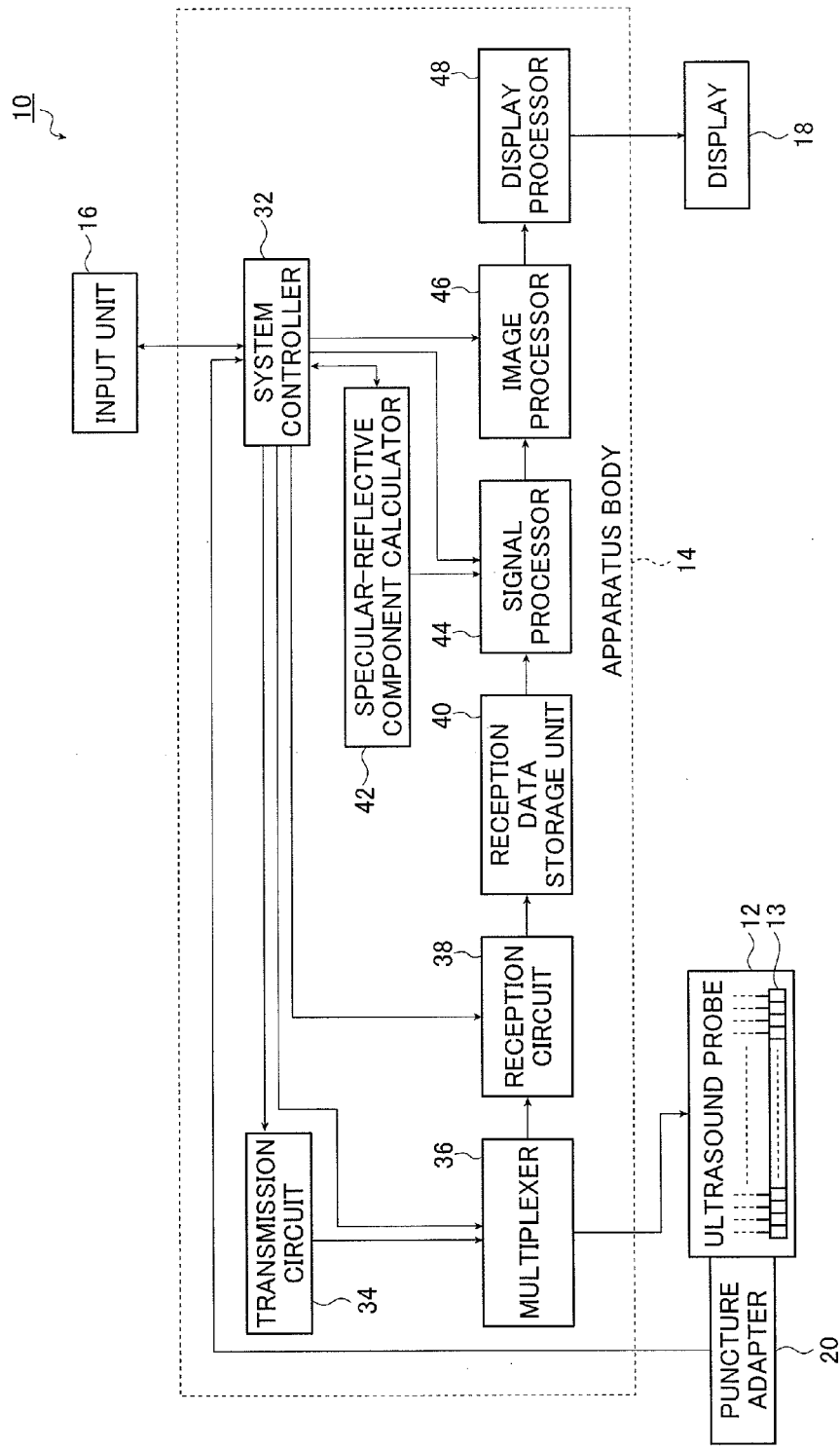
FIG. 2 is a block diagram showing the main configuration of the ultrasound diagnostic apparatus shown in FIG. 1.

FIG. 2 is a block diagram showing an example of the main configuration of an ultrasound diagnostic apparatus body of the ultrasound diagnostic apparatus shown in FIG. 1 and peripheral devices. The description of the configuration which has already been shown in FIG. 1 and described above will not be provided.

The apparatus body 14 includes a system controller 32, a transmission circuit 34, a multiplexer 36, a reception circuit 38, a reception data storage unit 40, a specular-reflective component calculator 42, a signal processor 44, an image processor 46, and a display processor 48.

The system controller 32 controls the entire ultrasound diagnostic apparatus 10 to perform an appropriate operation.

Specifically, the system controller 32 sequentially sets, through the transmission circuit 34 and the reception circuit 38, the transmission direction of an ultrasonic beam and the reception direction of an ultrasonic echo with straightness in the probe 12 maintained. The system controller 32 has a transmission control function of selecting a transmission delay pattern in accordance with the set transmission direction and a reception control function of selecting a reception delay pattern in accordance with the set reception direction.

The transmission delay pattern is the pattern of delay time which is imposed to the activation signal of each ultrasound transducer 13 so as to form an ultrasonic beam in a desired direction by ultrasonic waves transmitted from a plurality of ultrasound transducers 13. The reception delay pattern is the pattern of delay time which is imposed to the reception signal so as to extract an ultrasonic echo from a desired direction by ultrasonic waves received by a plurality of ultrasound transducers 13. A storage device which is attached to the system controller 32 stores a plurality of transmission delay patterns and a plurality of reception delay patterns distinguished from each other, and a plurality of transmission delay patterns and a plurality of reception delay patterns are selectively used depending on desired transmission direction and reception direction.

The system controller 32 controls the multiplexer 36 which sets transmit apertures constituted by a plurality of ultrasound transducers 13 for transmission and receive apertures constituted by a plurality of ultrasound transducers 13 for reception. According to this embodiment, the receive apertures and transmit apertures are set so as to be different such, for example, that the receive apertures are larger than the transmit apertures.

The system controller 32 outputs the puncture adapter information (the insertion angle and the like) notified from the input unit 16 or the puncture adapter 20 to the specular-reflective component calculator 42. The system controller 32 may read out the puncture adapter information from the storage unit of the puncture adapter 20 in advance to store the puncture adapter information in the storage device of the system controller 32, and read out the puncture adapter information as necessary to output to the specular-reflective component calculator 42.

The system controller 32 outputs a reception delay pattern to the signal processor 44 which performs a reception focus process.

The transmission circuit 34 includes a plurality of circuits corresponding to the maximum number of transmit apertures, and produces a plurality of activation signals which are respectively applied to a plurality of ultrasound transducers 13 set as transmit apertures through the multiplexer 36 by the system controller 32. At this time, it is possible to give the delay time to each of a plurality of activation signals on the basis of a transmission delay pattern selected by the system controller 32. The transmission circuit 34 adjusts the delay amount of each of a plurality of activation signals such that ultrasonic waves transmitted from a plurality of ultrasound transducers 13 set as transmit apertures form an ultrasonic beam, and supplies the activation signals to the probe 12.

The multiplexer 36 includes a group of a number of switches, is controlled by the system controller 32, and switches a plurality of ultrasound transducers set as transmit apertures or receive apertures.

With the switching of the multiplexer 36, an ultrasound transducer group to be used (for example, maximum 96, and in a normal use, 64) from among N (for example, 192) ultrasound transducers 13 of the probe 12 is selected and set as transmit apertures or receive apertures, and delivery of a transmission signal from the transmission circuit 34 to the probe 12 and delivery of a reception signal from the probe 12 to the reception circuit 38 are performed. Specifically, the multiplexer 36 is connected to N ultrasound transducers of the probe 12 through N signal lines. The multiplexer 36 is used for electronic scan, and the ultrasound transducers 13 are appropriately selected as transmit apertures or receive apertures to determine the position and direction where an ultrasonic beam is scanned.

The reception circuit 38 includes a plurality of circuits corresponding to a maximum number of receive apertures (for example, 96). The reception circuit 38 receives and amplifies a plurality of analog reception signals output from a plurality of ultrasound transducers 13 set as receive apertures through the multiplexer 36 by the system controller 32, and converts the analog reception signals to digital reception signals (reception data).

Digital-converted reception data is sequentially stored in the reception data storage unit 40 which has memory capacity for accumulating reception signal data corresponding to an ultrasound image for a plurality of frames.

The reception data storage unit 40 has a function as storage means for storing reception data (RAW data) output from the reception circuit 38, and appropriately outputs reception data to the signal processor 44 on the basis of a read instruction from the signal processor 44.

The specular-reflective component calculator 42 calculates information relating to a specular-reflective component on the puncture needle in an ultrasonic beam transmitted from the probe 12 described below on the basis of the puncture adapter information provided from the system controller 32, and supplies the result (the calculated information relating to the specular-reflective component) to the system controller 32 and the signal processor 44.

The signal processor 44 performs a reception focus process in which the delay time is given to each of a plurality of pieces of reception data on the basis of a reception delay pattern selected by the system controller 32, and these pieces of reception data are added. With this reception focus process, the focus of an ultrasonic echo is narrowed to form reception data (sound ray data).

Next, the signal processor 44 performs a detection process, such as an envelope detection process or a quadrature detection process, on sound ray data, and then corrects attenuation depending on the distance in accordance with the depth of the reflection position of the ultrasonic wave by STC (Sensitivity Time gain Control).

The image processor 46 produces image data representing a B-mode image and outputs image data to the display processor 48. Specifically, the image processor 46 subjects sound ray data read out from the signal processor 44 to a preprocess, such as logarithmic compression or gain adjustment, and a scan line conversion process for converting sound ray data to image data based on a normal television signal scan system to produce a B-mode image.

The display processor 48 produces a video signal for displaying a screen on the display 18 and outputs the video signal to the display 18.

The display 18 displays a screen including an ultrasound image output from the display processor 48, a measurement result, and the like to provide various kinds of information to the operator.

Next, the outline and principle of the operation of the ultrasound diagnostic apparatus 10 of this embodiment, and the method of transmitting and receiving an ultrasonic wave according to the invention will be described.

Figure 3:
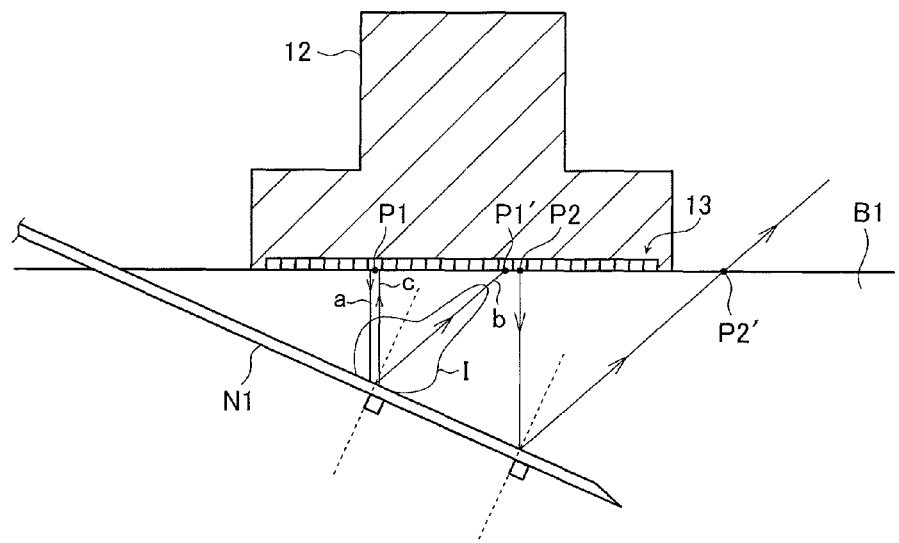
FIG. 3 is a schematic view showing the geometric relationship between a transmitted ultrasonic wave and a reflected ultrasonic wave in an ultrasound probe of the related art.

FIG. 3 is a schematic view showing the geometric relationship between a transmitted wave and a reflected wave of an ultrasonic wave in an ultrasound probe of the related art. For simplification of description, it is shown that there is no refraction in the body surface of a subject B1 (the same applied to the subsequent drawings).

The puncture needle is formed of metal and is significantly different in acoustic impedance from surrounding subject tissues. For this reason, it is considered that an image of the puncture needle is prominently obtained in an ultrasound image. However, actually, if an ultrasound image is captured, the puncture needle does not form an image so as to be distinguished from other tissues. To the contrary, there are many cases where the puncture needle is intermittently viewed. Accordingly, the inventors have conducted careful studies and have found the followings.

That is, as shown in FIG. 3, if ultrasonic waves transmitted from a plurality of ultrasound transducers 13 of the probe 12 toward the subject B1 enter the subject B1, abut on a puncture needle N1, and are specularly reflected by the puncture needle N1, there is a situation in which reflected waves are out of the reception range of the probe 12. For example, an ultrasonic wave transmitted from P1 enters the subject B1 in an incident wave direction indicated by a reference sign "a" in FIG. 3 and is reflected by the puncture needle N1 in specular reflection in a direction indicated by a reference sign "b" in FIG. 3, while the reflected wave having an intensity distribution indicated by a reference sign "I" in FIG. 3 is received at P1'. A normal ultrasonic echo signal reflected by a subject tissue travels in a direction indicated by a reference sign "c" in FIG. 3 and is received at P1.

However, an ultrasonic wave transmitted from P2 is specularly reflected by the puncture needle N1, reaches P2', and is thus out of the reception range of the probe 12. From this, the phenomenon in which, if a part or the whole of a reflected wave escapes and does not reach the probe 12, an image of the puncture needle N1 in an ultrasound image is difficult to view will be described.

In general, it is postulated that, in an ultrasound diagnostic technique in which a tissue of an organism is postulated as a subject, a normal ultrasonic echo signal (for example, having a point-reflective component) which is obtained when an ultrasonic wave is reflected by the tissue of the organism is received, and an image is formed from the ultrasonic echo signal. However, in general, the puncture needle is a metallic body, and the surface thereof is smooth. In this case, it is predicted that the reflection characteristic of an ultrasonic wave in the surface of the puncture needle is significantly different from the tissue of the organism, and specular reflection is prominent. Since ultrasonic waves emitted from a plurality of ultrasound transducers of the ultrasound probe are specularly reflected in the smooth surface of the puncture needle, in the ultrasound diagnostic apparatus of the related art, when a signal in which a normal ultrasonic echo signal (also referred to as a point-reflective component) reflected from the tissue of the organism and a specular-reflective component specularly reflected from the surface of the puncture needle are superimposed is received using the ultrasound probe arranged in the body surface of the organism as a subject to simultaneously collect information regarding the tissue of the organism and information regarding the tip portion of the puncture needle, it is difficult to constantly observe the tip portion of the puncture needle as a clear image on ultrasound image data.

Accordingly, with regard to the ultrasound diagnostic apparatus which can catch a reflected wave reaching P2' in FIG. 3, the inventors have obtained the following findings. First, the first finding resides in that an ultrasound probe having a long reception range compared to the related art, specifically, an ultrasound probe in which an array portion with ultrasound transducers arranged therein is long compared to the related art is manufactured. However, this is not sufficient. For example, although an ultrasound probe having 256 ultrasound transducers has a comparatively long array portion, in a normal method of transmitting and receiving an ultrasonic wave, there are many cases where, with regard to single transmission and reception, only 64 ultrasound transducers corresponding to ¼ of 256 are used to set 64 channels, or a shorter number of channels may be set.

Accordingly, an intrinsic problem does not refer to the length of the array portion but to whether or not the range in which ultrasonic waves transmitted from transmit apertures set on a plurality of ultrasound transducers of the ultrasound probe and specularly reflected on the surface of the puncture needle are predicted to reach is covered by receive apertures set on a plurality of ultrasound transducers of the ultrasound probe. Accordingly, the second finding of the inventors resides in that the range in which a specularly reflected wave reaches is predicted, and the receive apertures of the ultrasound probe are set so as to be different from the transmit apertures, e.g., larger than the transmit apertures, on the basis of the prediction result, so that the ultrasound probe can cover (receive) a specularly reflected wave. The transmit apertures and the receive apertures are set on a plurality of ultrasound transducers, and mean the positions of the ultrasound transducer and the number of ultrasound transducers (the number of channels) for reception.

The specularly reflected wave (also referred to as a specular-reflective component) from the puncture needle is to be only taken into account in order to only obtain the image of the puncture needle. To begin with, since paracentesis is an action where there is an object (subject tissue) of paracentesis, and the puncture needle is inserted toward the object, it is important to obtain images of the object of paracentesis and surrounding tissues. In this case, it is necessary for an ultrasound diagnostic apparatus not only to cover the specular-reflective component of the puncture needle but also to sufficiently receive the normal ultrasonic echo signal reflected from the normal subject tissue.

Figure 4:
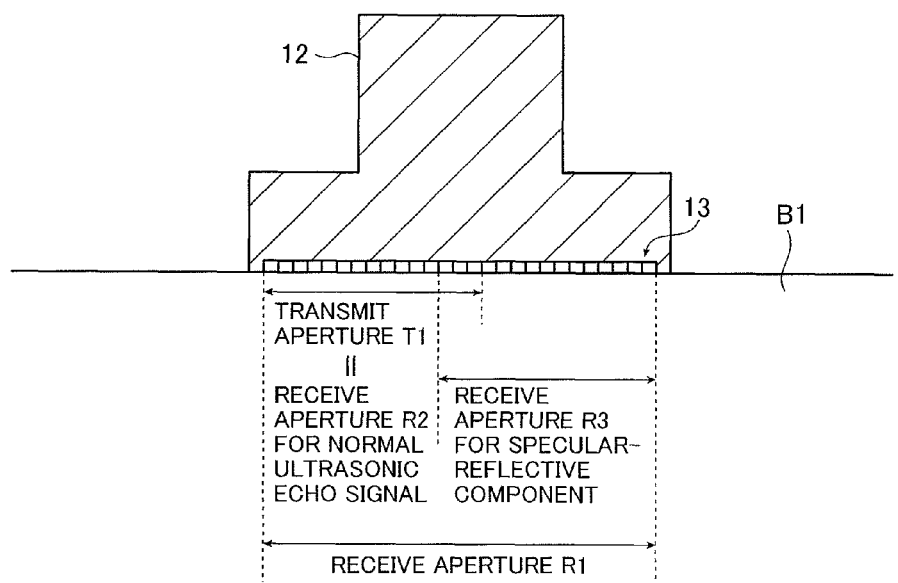
FIG. 4 is a schematic view illustrating the basic concept of a method of transmitting and receiving an ultrasonic wave in an embodiment of the invention.

FIG. 4 is a schematic view illustrating the basic concept of a method of transmitting and receiving an ultrasonic wave according to an embodiment of the invention which is executed by the ultrasound diagnostic apparatus of this embodiment.

FIG. 4 shows a transmit aperture T1 and a receive aperture R1 of the probe 12, and similarly to an ultrasound diagnostic apparatus of the related art, a receive aperture R2 for receiving the normal ultrasonic echo signal (point-reflective component) reflected from a subject tissue or the like coincides with the transmit aperture T1. Meanwhile, a receive aperture R3 for receiving the specular-reflective component from the puncture needle N1 does not coincide with the transmit aperture T1 and is expanded rightward in FIG. 4. More specifically, the receive aperture R3 is set so as to include those of the ultrasound transducers 13 located on the opposite side with respect to the transmit aperture T1 from the insertion position at which the puncture needle N1 is inserted into the subject B1, so that the receive aperture R3 is set on two or more of the ultrasound transducers 13 located in positions to receive the specular-reflective component of the ultrasonic beam reflected by the puncture needle N.

In the method of transmitting and receiving an ultrasonic wave of this embodiment, a synthetic aperture in which both the receive aperture R2 for the normal ultrasonic echo signal and the receive aperture R3 for the specular-reflective component are combined is the receive aperture R1. Thus, the receive aperture R1 extends more toward the opposite side with respect to the transmit aperture T1 from the insertion position of the puncture needle N1 into the subject B1 as compared with the type known in the art. In this way, the apparatus body 14 uses a mode in which the position and width (the number of channels) of the receive aperture R1 of the probe 12 are changed in accordance with the specular-reflective component of the puncture needle.

Although only the normal ultrasonic echo signal substantially reaches the receive aperture R2 for the normal ultrasonic echo signal, it will be obvious that the specular-reflective component and the normal ultrasonic echo signal reach the receive aperture R3 for the specular-reflective component.

Figure 5:
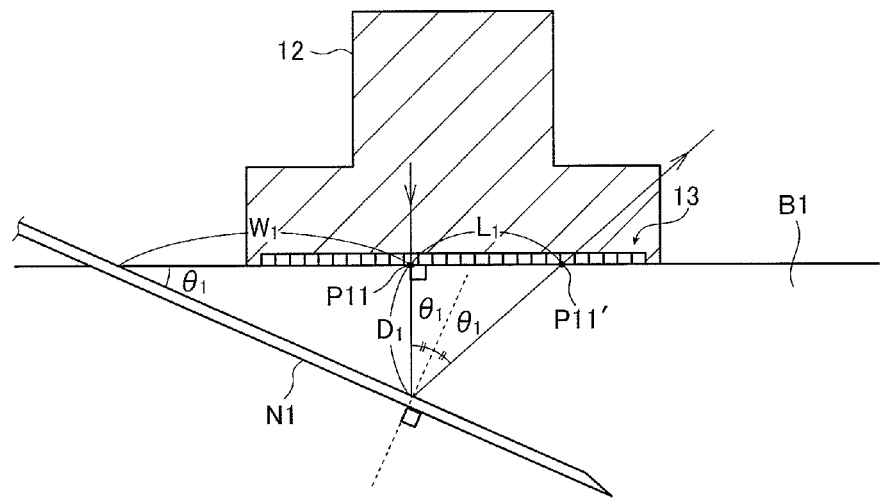
FIG. 5 is a schematic view illustrating the outline of an example of a method of transmitting and receiving an ultrasonic wave according to an embodiment of the invention.

FIG. 5 is a schematic view showing an example of a method of predicting a range where an ultrasonic wave specularly reflected on the puncture needle reaches in this embodiment.

If the insertion angle of the puncture needle N1 into the subject B1 is $\theta_1$, the center position of an ultrasound transmission beam is P11, the depth from the surface of the subject B1 to the puncture needle N1 at the center position P11 is $D_1$, a point at which a reflected wave is received by the ultrasound transducer after specular reflection occurs on the puncture needle N1 at the depth $D_1$ from the center position P11 of the ultrasound transmission beam is P11', and the distance from the center position P11 of the ultrasound transmission beam to the insertion position of the puncture needle is $W_1$, the distance $L_1$ between the point P11' to which a reflected wave returns and the center position P11 of the transmission beam is calculated by Expression (1).

$$L_1 = D_1 \tan 2\theta_1 \quad (1)$$
$$= W_1 \tan\theta_1 \tan 2\theta_1$$

Accordingly, it is preferable to determine the width of the receive aperture taking into consideration the point P11' to which a reflected wave returns. For example; in the normal transmission and reception without taking into consideration the puncture needle N1, the transmit aperture T1 and the receive aperture R2 (see FIG. 4) are set in 64 elements, and when receiving an echo signal based on a reflected wave of the puncture needle N1, the receive aperture R1 (see FIG. 4) is extended toward the reaching point P11' of the reflected wave to set the number of receive apertures to, for example, the maximum number, say 96 elements. In particular, when an ultrasound transmission beam is formed on the rightmost end of the transmit aperture, a point at the rightmost end to which a reflected ultrasonic wave of the ultrasound transmission beam returns is a critical point, and in a best state, the receive aperture covers this point.

When it is also necessary to take into consideration the influence of refraction in the body surface of the subject B1 or inside the subject B1, it is preferable to perform calculation in accordance with the Snell's law.

Information necessary for determining the width of the receive aperture, for example, in the above-described example, positional information of the point P11' to which a reflected wave returns is produced as specular-reflective component information in the specular-reflective component calculator 42. The signal processor 44 determines a method of processing reception data from the reception data storage unit 40 on the basis of this information, and the system controller 32 controls a switching method in the multiplexer 36.

Figure 6:
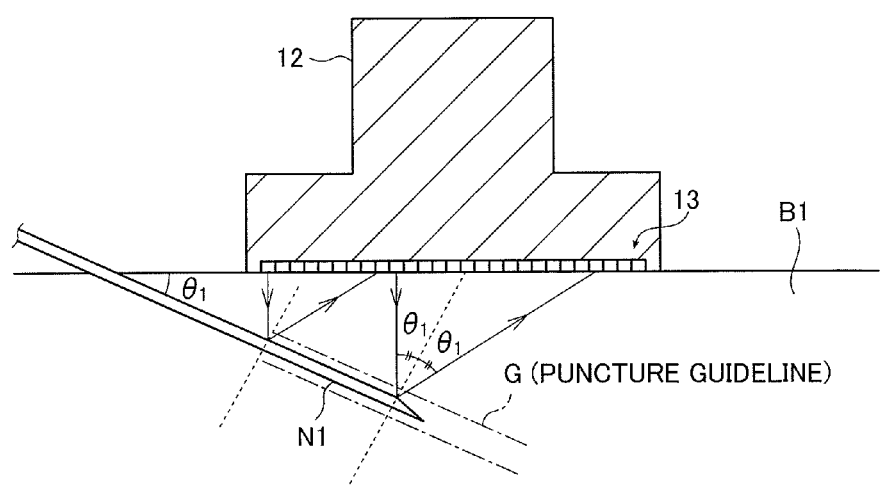
FIG. 6 is a schematic view illustrating an example of an ultrasound probe, a puncture guideline, and a specularly reflected ultrasonic wave from a puncture needle displayed on a display in a method according to an embodiment of the invention.

The insertion angle $\theta_1$ of the puncture needle N1 into the ultrasound transducer array is supplied from the system controller 32 to the specular-reflective component calculator 42 as puncture adapter information. When the puncture adapter 20 is attached to the probe 12, as shown in FIG. 6, a puncture guideline G which is used to guide the puncture needle N1 may be displayed on the display 18, and the insertion angle $\theta_1$ of the puncture needle N1 may be known to the technician as an angle between the puncture guideline G and the surface of the subject B1.

Though not shown, the apparatus body 14 may be separately provided with a puncture needle detector so that the insertion angle is determined on the basis of positional information of the puncture needle which is automatically recognized by the puncture needle detector on the basis of the ultrasound image and is output from the puncture needle detector.

As described above, in the ultrasound diagnostic apparatus and the method of transmitting and receiving an ultrasonic wave according to Embodiment 1 of the invention, the width of the receive aperture (the number of channels) is determined on the basis of the positional relationship between the puncture needle and the ultrasound probe, and beam forming is performed for a reception signal obtained in the corresponding receive aperture. Accordingly, since it is possible to improve display resolution of an ultrasound image including the inserted puncture needle, visibility of the puncture needle is improved. The most important parameter of information representing the positional relationship between the puncture needle and the ultrasound probe is the angle between the traveling direction of a transmitted ultrasonic wave and the puncture-needle, that is, the insertion angle of the puncture needle.

In this embodiment, a mode has been described where the receive aperture is expanded compared to that in the related art in order to receive the specular-reflective component and the normal ultrasonic echo signal (point-reflective component). However, for example, when weight is not given to the normal ultrasonic echo signal, a mode may be used in which the position of the receive aperture is changed on the basis of specular-reflective component information.

Although in this embodiment, a case has been described where the width of the receive aperture is changed (for example, a change from 64 elements to 96 elements), the position of the receive aperture may be changed such that the center position in the transmission beam direction and the reaching position of the specular-reflective component from the puncture needle are contained in the receive aperture. The receive aperture for receiving an ultrasonic echo from the transmission beam direction and the receive aperture for the reaching position of the specular-reflective component from the puncture needle may be separately set.

Embodiment 2

An ultrasound diagnostic apparatus according to Embodiment 2 of the invention has a reception apodization function added to the signal processor 44 of the apparatus body 14 of the ultrasound diagnostic apparatus 10 in Embodiment 1. The configuration of the ultrasound diagnostic apparatus of this embodiment is substantially the same as the ultrasound diagnostic apparatus 10 shown in FIGS. 1 and 2, except the reception apodization function, and thus description in connection with the drawings will not be provided. Hereinafter, in the detailed description of the ultrasound diagnostic apparatus of this embodiment, the same components as those of the ultrasound diagnostic apparatus 10 shown in FIG. 2 are denoted by the same reference numerals.

Reception apodization is a technique which gives weighting factors to a plurality of pieces of reception data before an addition process is performed. Specifically, the largest weight is set for a reception signal from an ultrasound transducer at the center of an ultrasonic beam, and a smaller weight is set for a reception signal with an increasing distance from the center. Thus, it is possible to perform a reception process while a reception signal directly reaching from a target under observation which will be at the center of the ultrasonic beam is most highlighted, such that a received ultrasonic beam can have high precision.

Figure 7A:
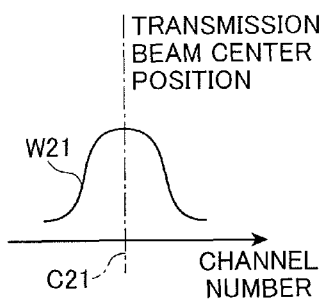
FIG. 7A is a schematic view illustrating a method of transmitting and receiving an ultrasonic wave of the related art in an ultrasound diagnostic apparatus of the related art.
Figure 7B:
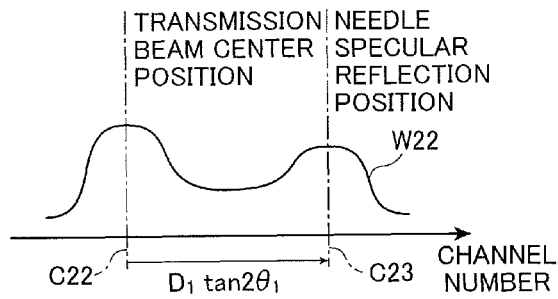
FIG. 7B is a schematic view illustrating the outline of another example of a method of transmitting and receiving an ultrasonic wave in an ultrasound diagnostic apparatus according to an embodiment of the invention.

FIG. 7A is a schematic view showing a method of transmitting and receiving an ultrasonic wave of the related art which is executed by an ultrasonic diagnostic apparatus of the related art. FIG. 7B is a schematic view showing the outline of an example of a method of transmitting and receiving an ultrasonic wave of this embodiment which is executed by the ultrasound diagnostic apparatus of this embodiment. FIG. 7A shows the outline of reception apodization of the related art. Usually, the peak of a weighting curve W21 of reception apodization and the center position C21 of a transmission beam are set to coincide with each other.

FIG. 7B shows the outline of reception apodization of this embodiment. As will be understood from FIG. 7B, in this embodiment, a weighing curve W22 of reception apodization has two peaks. One peak is set to coincide with the center position C22 of the transmission beam, and another peak is set at the center position C23 of the specular-reflective component from the puncture needle. The center position C23 of the specular-reflective component is set at a position distant from the center position C22 of the transmission beam by $D_1 \tan 2\theta_1$ by Expression (1). The reception apodization process is performed before the addition process in the reception focus process by the signal processor 44 of the apparatus body 14 shown in FIG. 2.

In this way, with regard to the weight setting by reception apodization, two peaks, that is, two sites where a reception signal is to be highlighted are set, thereby obtaining an image of a subject tissue with high precision and also obtaining an image of a puncture needle with high precision.

As described above, according to the ultrasound diagnostic apparatus of this embodiment, reception apodization is performed on both the transmission beam center position and the reaching position of the specular-reflective component on the puncture needle. Therefore, it is possible to perform a highlight process on reception signals of both targets under observation and to further improve display resolution of an ultrasound image including the inserted puncture needle.

Although in this embodiment, a mode has been described in which two peaks are set by the weight setting through reception apodization, for example, when weight is not given to the normal ultrasonic echo signal (point-reflective component) from the subject tissue, a mode in which a peak is set for only the specular-reflective component may be used.

In FIG. 7B, a mode has been described in which two peaks draw the same normal curve in the weighting curve W22 of reception apodization. However, a case where a weighting curve is different between the subject tissue and the puncture needle is also considered and therefore a weighting curve appropriate for the needle may be applied to the specular-reflective component.

Although the weighting curve W22 having two peaks is used in the embodiment shown in FIG. 7B to effect reception apodization for both the transmission beam center position and the position at which the specular-reflective component arrives from the puncture needle, the invention is not limited thereto; to effect reception apodization for the individual positions, a weighting curve having a single peak may be used for each of these positions.

Figure 8:
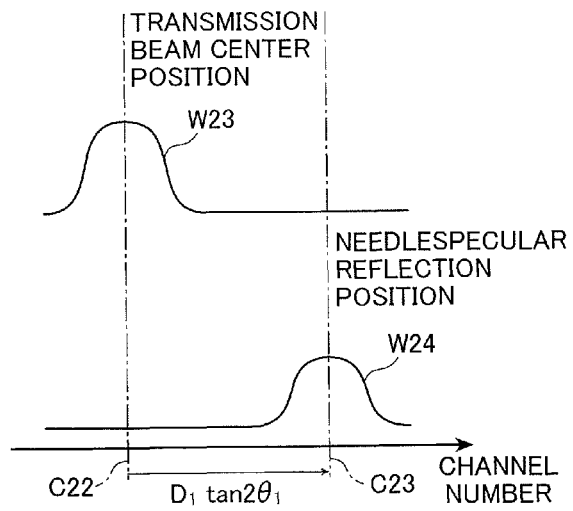
FIG. 8 is a schematic view illustrating the outline of another example of a method according to an embodiment of the invention.

An embodiment shown in FIG. 8, for example, uses a weighting curve W23 having a single peak so set as to coincide with the transmission beam center position C22 to effect reception apodization for the transmission beam center position and a weighting curve W24 having a single peak so set as to coincide with the center position C23 of the specular-reflective component reflected by the puncture needle to effect reception apodization for the position at which the specular-reflective component reflected by the puncture needle arrives.

Accordingly, since the reception data containing the normal ultrasonic echo signal from the subject tissue (hereinafter referred to also as subject tissue component) and the specular-reflective component from the puncture needle are stored in the reception data storage unit 40 in this embodiment, the signal processor 44 effects reception apodization for enhancing the subject tissue component using the weighting curve W23 (subject tissue enhancement processing) and reception apodization for enhancing the specular-reflective component from the puncture needle using the weighting curve W24 (specular-reflective component enhancement processing) for the same reception data stored, and the image processor 46 synthesizes the individually enhanced reception data. Enhancement processing such as filtering processing may be performed before the synthesis. Thus, optimal image processing for the subject tissue component and the specular-reflective component from the puncture needle is made possible as the same reception data stored in the reception data storage unit 40 is used repeatedly.

The weighting curves W23 and W24 used for reception apodization are examples each having a peak exhibiting a normal curve similar to each other but the invention is not limited thereto; the peaks may differ, provided that the weighting curves used are appropriate for the subject tissue component and the specular-reflective component from the puncture needle.

Embodiment 3

An ultrasound diagnostic apparatus according to Embodiment 3 of the invention has an aperture synthesis function different from that of Embodiment 1 added to the apparatus body 14 of the ultrasound diagnostic apparatus 10 in Embodiment 1. The configuration of the ultrasound diagnostic apparatus of this embodiment is substantially the same as that of the ultrasound diagnostic apparatus 10 shown in FIGS. 1 and 2, except that the aperture synthesis function is different, and thus description in connection with the drawings will not be provided. Hereinafter, in the detailed description of the ultrasound diagnostic apparatus of this embodiment, the same components as those of the ultrasound diagnostic apparatus 10 shown in FIG. 2 are denoted by the same reference numerals.

The aperture synthesis technique for use in this embodiment is the technique which is described in commonly assigned JP 2010-29374 A. Specifically, according to this technique, an ultrasonic beam is transmitted multiple times, ultrasonic echo signals generated are received by a plurality of ultrasound transducers in a plurality of different receive apertures, reception signals are temporarily stored in a memory, reception signals obtained in different receive aperture are synthesized, and a reception focus process is performed on a resultant reception signal.

Figure 9:
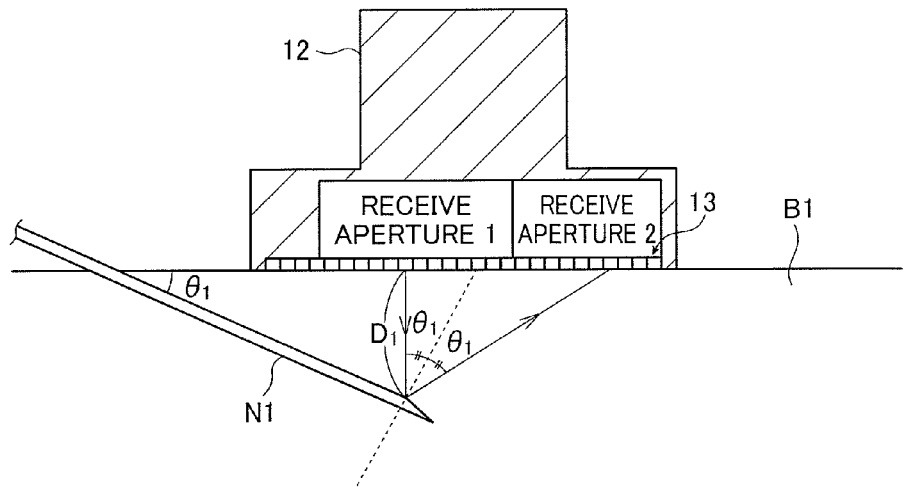
FIG. 9 is a schematic view illustrating the outline of another example of a method according to an embodiment of the invention.

FIG. 9 is a schematic view illustrating the outline of an example of a method of transmitting and receiving an ultrasonic wave of this embodiment which is executed by the ultrasound diagnostic apparatus of this embodiment. In this embodiment, a transmit aperture and a receive aperture 1 coincide with each other, and an ultrasonic beam transmitted from the transmit aperture is specularly reflected by the puncture needle N1. In the case of FIG. 9, the ultrasonic beam returns to a receive aperture 2, not the receive aperture 1. For this reason, when it is determined that an aperture synthesis process should be performed in the ultrasound diagnostic apparatus of this embodiment, an ultrasonic beam is transmitted using the same transmit aperture twice. In the first reception, a reception process is performed in the receive aperture 1 to temporarily store reception data in the reception data storage unit 40, and in the second reception, the ultrasound transducers 13 are switched by the multiplexer 36, and a signal is received in the receive aperture 2. Thereafter, the signals obtained in the two receptions in total are synthesized.

In the ultrasound diagnostic apparatus of this embodiment, the determination of whether or not the aperture synthesis process should be performed is made by the system controller 32 on the basis of specular-reflective component information provided from the specular-reflective component calculator 42. Specifically, the system controller 32 determines that the aperture synthesis of the receive aperture 1 and the receive aperture 2 will be performed when Expression (2) is satisfied such that the normal ultrasonic echo signal (point-reflective component) from the transmission beam direction and the specular-reflective component from the puncture needle N1 are received with a sufficient receive aperture width.

$$D_1 \tan 2\theta_1 \geq (\text{receive aperture width})/2 \quad (2)$$

In the aperture synthesis process, the transmission process of an ultrasonic beam multiple times is realized when the system controller 32 controls the multiplexer 36 and the transmission circuit 34. In the aperture synthesis process, the reception process by a plurality of different apertures is realized when the system controller 32 controls the multiplexer 36, the reception circuit 38, the reception data storage unit 40, and the signal processor 44. The signal processor 44 performs a corresponding reception focus process on reception data sent from a reception system, such as the reception circuit 38, to obtain aperture-synthesized reception data.

As described above, according to the ultrasound diagnostic apparatus of this embodiment, element data of the receive aperture 1 where the normal ultrasonic echo signal (point-reflective component) from the subject tissue B1 is prominent and element data of the receive aperture 2 where the specular-reflective component from the puncture needle N1 is prominent are subjected to aperture synthesis, thereby obtaining reception signals of both targets under observation and also further improving display resolution of an ultrasound image including the inserted puncture needle.

Embodiment 4

The ultrasound diagnostic apparatus according to Embodiment 4 of the invention has an aperture synthesis function different from that of Embodiment 3 added to the apparatus body 14 of the ultrasound diagnostic apparatus 10 described in Embodiment 1. As described above, different from above Embodiment 3, the receive apertures according to this embodiment correspond to those of the above Embodiment 1 as divided into receive apertures for receiving an ultrasonic echo signal from the transmission beam direction (point-reflective component) and receive apertures for the position at which the specular-reflective component reflected by the puncture needle arrives for one transmission. Similar descriptions therefore will be omitted and differences will mostly be described.

Figure 10:
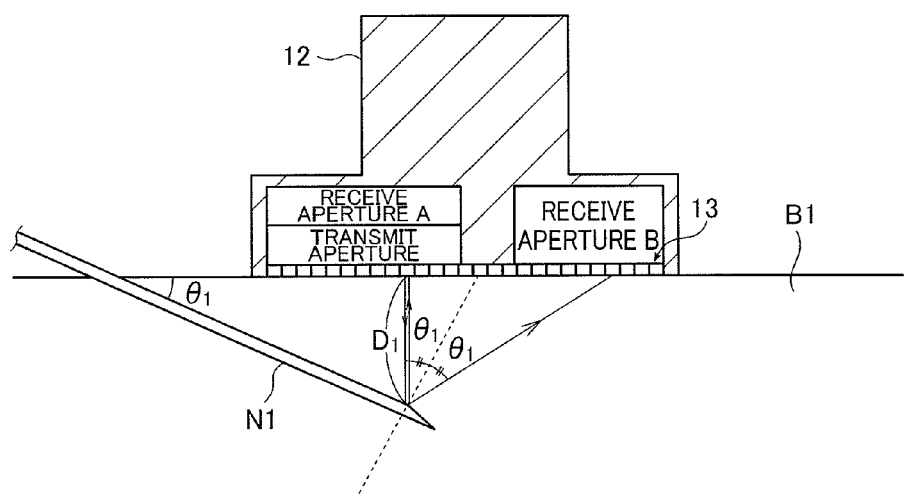
FIG. 10 is a schematic view illustrating the outline of another example of a method according to an embodiment of the invention.

FIG. 10 is a schematic view illustrating the outline of an example of the method of transmitting and receiving an ultrasonic wave according to this embodiment implemented by the ultrasound diagnostic apparatus of this embodiment.

The receive apertures set in this embodiment are a receive aperture A centered on the transmission direction and a receive aperture B centered on the ultrasound transducers for the specular-reflective component, the receive apertures A and B being divided from each other by at least one ultrasound transducer 13 not used as receive aperture, each of these receive apertures A and B including a plurality of ultrasound transducers 13.

According to this embodiment, the transmit apertures and the receive aperture A coincide, and the ultrasonic beam transmitted from the transmit apertures is reflected by a normal subject tissue and returned to the receive aperture A as normal ultrasonic echo signal (point-reflective component), while the specularly reflected wave (specular-reflective component) reflected by the puncture needle N1 in specular reflection (mirror reflection) is returned not to the receive aperture A but to the receive aperture B. Thus, in the ultrasound diagnostic apparatus according to this embodiment, a normal ultrasonic echo signal can be received by the receive aperture A, and the specular-reflective component from the puncture needle N1 can be received by the receive aperture B. According to this embodiment, the transmit apertures and the receive aperture A need not necessarily coincide.

Thus, according to this embodiment, ultrasonic echo signals received by the two receive apertures A and B are synthesized, that is, aperture synthesis processing by the receive aperture A and the receive aperture B is performed, to synthesize the images of the subject tissue B1 and the puncture needle N1.

The reason for locating at least one element of the ultrasound transducers 13 not used as receive aperture between the receive aperture A and the receive aperture B is to ensure that a signal immediately beneath a transmit aperture where a normal image signal is strong and a signal where the specular-reflective component from the puncture needle is strong are received, one distinctly separate from the other even with a portable low-cost type having only a small number of elements in a reception circuit.

According to this invention, since a normal ultrasonic echo signal and the specular-reflective component from the puncture needle N1 in one transmission of the ultrasonic beam can be received by the two divided receive apertures A and B, an apparatus having only a small number of channels can receive the specular-reflective component. Settings of the two divided receive apertures A and B on a number of ultrasound-transducers 13 can be readily made by the multiplexer 36.

According to this embodiment, an image with an enhanced puncture needle visibility can be provided without lowering the frame rate, which is important when the puncture needle is inserted, by temporarily storing the reception echo signal as reception data (reception data received by the individual ultrasound transducers 13, which may also be referred to simply as element data below) in the reception data storage unit 40, performing reception beam forming in two or more directions including the transmission beam direction and the puncture needle specular-reflection direction from the element data in one transmission, and synthesizing and displaying data of these, ultrasonic echo signal data.

Thus, according to the above Embodiment 3, a plurality of ultrasonic beam transmission processings are performed and, for every transmitted ultrasonic beam, aperture synthesis processing is performed whereby a normal ultrasonic echo signal (point-reflective component) and a specular-reflective component from the puncture needle N1 are received by a plurality of different apertures and synthesized. According to this embodiment, on the other hand, the echo signals in the transmission beam direction and the puncture needle specular reflection direction can be received by the receive aperture A and the receive aperture B in one transmission, so that the frame rate is not lowered as compared with the above Embodiment 3 wherein the echo signals in the transmission beam direction and the puncture needle specular reflection direction are received by the receive aperture 1 and the receive aperture 2 respectively in a plurality of transmissions, and, moreover, there is no need to switch between the transmit apertures and the receive aperture 1, and the transmit apertures and the receive aperture 2 through the multiplexer 36 as required in the above Embodiment 3, thereby enabling easy and quick switching of the two receive apertures A and B by the multiplexer 36 from the transmit apertures. Thus, such problems as delay in switching timing that may possibly occur in the above Embodiment 3 can be eliminated.

Further, according to this embodiment, since the element data of the receive aperture A where the normal ultrasonic echo signal from the subject tissue B1 (point-reflective component) is a major component and the element data of the receive aperture B where the specular-reflective component from the puncture needle N1 is a major component are combined in the aperture synthesis processing, the reception signals of both subjects of observation can be obtained, thereby increasing the display resolution of an ultrasound image with an inserted puncture needle.

Embodiment 5

An ultrasound diagnostic apparatus according to Embodiment 4 of the invention is different from the ultrasound diagnostic apparatus 10 of Embodiment 1 in that the probe 12 has a function of transmitting an ultrasonic beam with a deflection angle (see FIG. 11), not in a direction perpendicular to the array direction of the ultrasound transducers 13. Except for this point, the ultrasound diagnostic apparatus of this embodiment is Substantially the same as the ultrasound diagnostic apparatus 10 shown in FIGS. 1 and 2, and thus description in connection with the drawings will not be provided. An apparatus body of the ultrasound diagnostic apparatus of this embodiment has a configuration corresponding to the novel function. Hereinafter, in the detailed description of the ultrasound diagnostic apparatus of this embodiment, the same components as those of the ultrasound diagnostic apparatus 10 shown in FIG. 2 are denoted by the same reference numerals.

Figure 11:
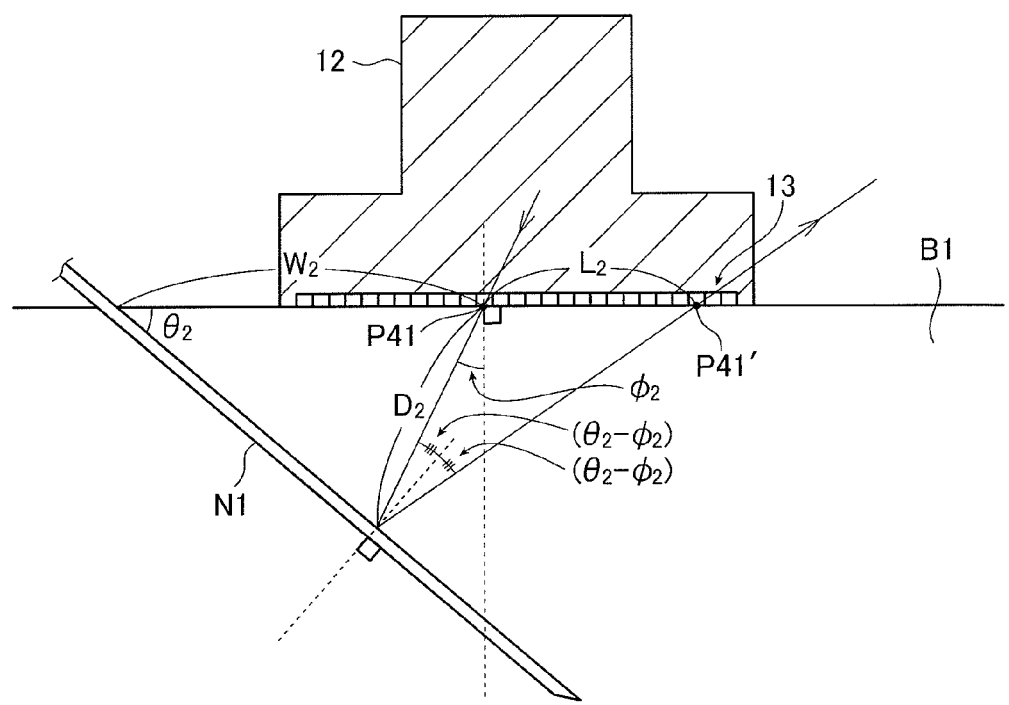
FIG. 11 is a schematic view illustrating the outline of another example of a method according to an embodiment of the invention.

FIG. 11 is a schematic view illustrating an example of a method of predicting a range in which, in an ultrasonic beam transmitted with a deflection angle, a specularly reflected wave (specular-reflective component) of an ultrasonic wave from a puncture needle reaches.

If the insertion angle of the puncture needle N1 into the subject B1 is $\theta_2$, a point at which a reflected wave is emitted from the subject B1 after an ultrasonic wave having entered at an inclination angle $\phi_2$ from an entrance position P41 of the ultrasonic wave caused specular reflection on the puncture needle N1 at a depth $D_2$ is P41', and the distance from the entrance position P41 of an ultrasonic wave to the insertion position of the puncture needle N1 is $W_2$, the distance $L_2$ between the point P41' to which the reflected wave returns and the entrance point P41 is calculated by Expression (3).

Accordingly, in the ultrasound diagnostic apparatus of this embodiment, it is preferable to determine the width of the receive aperture taking into consideration of the point P41' to which the reflected wave returns.

$$L_2 = D_2 \cdot \cos\phi_2\{\tan(2\theta_2 - \phi_2) - \tan\phi_2\} \quad (3)$$
$$= W_2 \cdot \frac{\tan\theta_2\{\tan(2\theta_2 - \phi_2) - \tan\phi_2\}}{\tan\theta_2 \cdot \tan\phi_2 + 1}$$
$$\left(W_2 = D_2 \cdot \frac{\cos\phi_2\{\tan\theta_2 \cdot \tan\phi_2 + 1\}}{\tan\theta_2}\right)$$

As described above, according to the ultrasound diagnostic apparatus and the apparatus body of this embodiment, even when an ultrasonic beam is transmitted from the ultrasound probe with an inclination angle, it is possible to determine the position and width (the number of channels) of the receive aperture on the basis of the positional relationship between the puncture needle and the ultrasound probe. Therefore, it is possible to improve display resolution of an ultrasound image including the inserted puncture needle, thereby improving visibility of the puncture needle.

Next, a method of transmitting and receiving an ultrasonic wave of the invention which is executed by the ultrasound diagnostic apparatus of the invention will be described.

Figure 12:
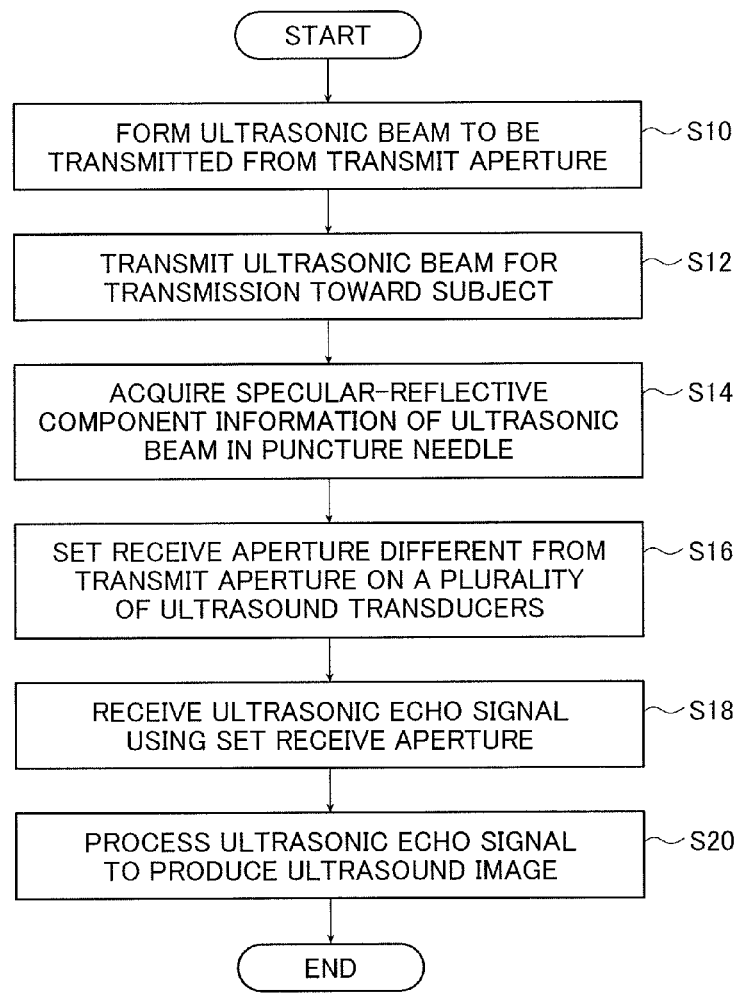
FIG. 12 is a flowchart showing an example of a method of transmitting and receiving an ultrasonic wave according to an embodiment of the invention.

FIG. 12 is a flowchart showing an example of a method of transmitting and receiving an ultrasonic wave according to the invention.

The method of transmitting and receiving an ultrasonic wave shown in FIG. 12 is executed in the ultrasound diagnostic apparatus 10 according to Embodiment 1 of the invention shown in FIGS. 1 and 2. As shown in FIGS. 4 to 6, a plurality of ultrasound transducers 13 of the probe 12 are used to perform transmission and reception of ultrasonic waves toward a target site of the subject B1 containing the puncture needle N1.

It is assumed that the operator powers on the apparatus body 14 of the ultrasound diagnostic apparatus 10, and abuts the probe 12 on the skin of the subject B1, such as a human subject.

First, in the method of transmitting and receiving an ultrasonic wave of the invention, in Step S10, an ultrasonic beam which is transmitted from a transmit aperture set on a plurality of ultrasound transducers 13 of the probe 12 is formed.

Next, in Step S12, the formed ultrasonic beam for transmission is transmitted toward the target site of the subject B1.

In Step S14, information relating to the specular-reflective component of the ultrasonic beam in the puncture needle N1 is acquired.

In Step S16, a receive aperture different from the transmit aperture is set on a plurality of ultrasound transducers 13 on the basis of the information relating to the specular-reflective component of the ultrasonic beam.

In Step S18, an ultrasonic echo signal of the ultrasonic beam is received by a plurality of ultrasound transducers 13 using the set receive aperture.

Subsequently, in Step S20, the ultrasonic echo signal received by a plurality of ultrasound transducers 13 using the receive aperture is processed to produce an ultrasound image.

In this way, in the method of transmitting and receiving an ultrasonic wave of the invention, it is possible to reliably and thoroughly receive, from the receive aperture, the component of the ultrasonic beam transmitted from the transmit aperture and specularly reflected on the puncture needle. For this reason, in the method of the invention, it is possible to increase the intensity of an echo signal from the puncture needle and to improve visibility of the puncture needle.

The above-described embodiments of the invention are merely illustrative of the invention, and are not intended to limit the configuration of the invention. The ultrasound diagnostic apparatus and the method of transmitting and receiving an ultrasonic wave according to the invention are not limited to the above-described embodiments, and various changes may be made without departing from the object of the invention.

For example, although in the embodiments, a case has been described where the ultrasound diagnostic apparatus, the display, and the input unit are separately provided, the ultrasound diagnostic apparatus, the display, and the input unit may be provided as a single device.

Although the foregoing embodiment is configured by a central processing unit (CPU) and software which causes the CPU to perform various processes, these may be configured by hardware, such as digital circuits or analog circuits. Software is stored in an internal memory (not shown).

The algorithm of the method of transmitting and receiving an ultrasonic wave according to the invention is described in a programming language, and compiled as necessary. The program for transmitting and receiving an ultrasonic wave is stored in a memory (storage medium) and executed by information processing means of another ultrasound diagnostic apparatus. Therefore, it is possible to realize the same functions as those of the ultrasound diagnostic apparatus according to the invention.

That is, the program for transmitting and receiving an ultrasonic wave according to the invention causes a computer to execute a plurality of steps for transmitting and receiving an ultrasonic wave toward a site of a subject containing a puncture needle using a plurality of ultrasound transducers. The steps includes the steps of forming an ultrasonic beam to be transmitted from a transmit aperture set on a plurality of ultrasound transducers, transmitting the formed ultrasonic beam toward the target site of the subject, acquiring information relating to a specular-reflective component of the ultrasonic beam in a puncture needle, setting a first receive aperture different from the transmit aperture on a plurality of ultrasound transducers on the basis of the information relating to the specular-reflective component of the ultrasonic beam, receiving an ultrasonic echo signal of the ultrasonic beam by a plurality of ultrasound transducers using the set first receive aperture, and processing the ultrasonic echo signal received by a plurality of ultrasound transducers using the first receive aperture.

It will be obvious that the invention may be implemented as a computer readable recording medium having the program for transmitting and receiving an ultrasonic wave recorded thereon.

The ultrasound diagnostic apparatus, the method of transmitting and receiving an ultrasonic wave, and the program for transmitting and receiving an ultrasonic wave according to the embodiments of the invention can be used for the purpose of, for example, paracentesis in which the puncture needle is inserted into the subject while viewing the ultrasound image.

What is claimed is:

1. An ultrasound diagnostic apparatus comprising:
a plurality of ultrasound transducers which performs transmission and reception of ultrasonic waves toward a target site of a subject that contains a puncture needle;
a transmission computing unit configured to form an ultrasonic beam to be transmitted from a transmit aperture set on the plurality of ultrasound transducers;
an acquisition unit configured to acquire information that relates to a specular-reflective component of the ultrasonic beam in the puncture needle;
a reception computing unit configured to set a receive aperture different from the transmit aperture set on the plurality of ultrasound transducers on the basis of the information that relates to the specular-reflective component of the ultrasonic beam; and
a reception signal processor configured to process an ultrasonic echo signal received by the plurality of ultrasound transducers set as the receive aperture,
wherein the reception computing unit sets as the receive aperture a first receive aperture that receives the specular-reflective component of the ultrasonic beam from the puncture needle and a second receive aperture that receives a point-reflective component of the ultrasonic beam from a subject tissue, the first receive aperture being different from the second receive aperture, and
wherein the reception signal processor synthesizes a first ultrasonic echo signal of the specular-reflective component receiving through the first receive aperture and a second ultrasonic echo signal of the point-reflective component receiving through the second receive aperture in accordance with one transmission by the transmit aperture.

2. The ultrasound diagnostic apparatus according to claim 1,
wherein the acquisition unit is configured to acquire the information that relates to the specular-reflective component from a positional relationship between the plurality of ultrasound transducers and the puncture needle.

3. The ultrasound diagnostic apparatus according to claim 2,
wherein the acquisition unit is configured to acquire the information that relates to the specular-reflective component from an insertion angle of the puncture needle inserted into the subject with respect to the plurality of ultrasound transducers.

4. The ultrasound diagnostic apparatus according to claim 3,
   wherein the transmission computing unit forms the ultrasonic beam to be deflected, and
   the acquisition unit is configured to acquire the information that relates to the specular-reflective component from the insertion angle of the puncture needle and a deflection angle of the ultrasonic beam.

5. The ultrasound diagnostic apparatus according to claim 1,
   wherein the reception signal processor performs a weighting process to enhance the first ultrasonic echo signal of the specular-reflective component.

6. The ultrasound diagnostic apparatus according to claim 5,
   wherein the reception signal processor further has a storage unit which temporarily stores the first ultrasonic echo signal and the second ultrasonic echo signal, performs the weighting process to enhance the second ultrasonic echo signal of the point-reflective component, and synthesizes the second ultrasonic echo signal on which the weighting process has thus been performed and the first ultrasonic echo signal of the specular-reflective component on which the weighting process has been performed.

7. The ultrasound diagnostic apparatus according to claim 1,
   wherein the reception signal processor further has a storage unit which temporarily stores the first ultrasonic echo signal and the second ultrasonic echo signal.

8. The ultrasound diagnostic apparatus according to claim 1,
   wherein the reception computing unit sets the first receive aperture to contain ultrasound transducers located on a side opposite with respect to the transmit apertures from an insertion position at which the puncture needle is introduced into a subject.

9. The ultrasound diagnostic apparatus according to claim 1,
   wherein the reception computing unit sets the first receive aperture and the second receive aperture discontinuously divided on the plurality of ultrasound transducers, and
   wherein there is at least one ultrasound transducer not used as the receive aperture between the first and second receive apertures.

10. An ultrasound diagnostic apparatus comprising:
   a plurality of ultrasound transducers which performs transmission and reception of ultrasonic waves toward a target site of a subject that contains a puncture needle;
   a transmission computing unit configured to form an ultrasonic beam to be transmitted from a transmit aperture set on the plurality of ultrasound transducers;
   an acquisition unit configured to acquire information that relates to a specular-reflective component of the ultrasonic beam in the puncture needle;
   a reception computing unit configured to set a receive aperture different from the transmit aperture set on the plurality of ultrasound transducers on the basis of the information that relates to the specular-reflective component of the ultrasonic beam; and
   a reception signal processor configured to process an ultrasonic echo signal received by the plurality of ultrasound transducers set as the receive aperture,
   wherein the reception computing unit sets as the receive aperture a first receive aperture that receives the specular-reflective component of the ultrasonic beam from the puncture needle and a second receive aperture that receives a point-reflective component of the ultrasonic beam from a subject tissue, the first receive aperture being different from the second receive aperture, and
   wherein the reception signal processor synthesizes a first ultrasonic echo signal of the specular-reflective component receiving through the first receive aperture and a second ultrasonic echo signal of the point-reflective component receiving through the second receive aperture in accordance with multiple times of transmission by the transmit aperture.

* * * * *